United States Patent
D'Alessio

(10) Patent No.: US 8,912,230 B2
(45) Date of Patent: Dec. 16, 2014

(54) METHOD FOR TREATING CELL DEGENERATION USING AT LEAST ONE MOLECULE CAPABLE OF INHIBITING ADHESION MOLECULE EXPRESSION AND VASCULAR ENDOTHELIUM ACTIN FIBRE POLYMERIZATION

(75) Inventor: Patrizia D'Alessio, Paris (FR)

(73) Assignee: Aisa Therapeutics, Evry (FR)

( * ) Notice: Subject to any disclaimer, the term of this patent is extended or adjusted under 35 U.S.C. 154(b) by 966 days.

(21) Appl. No.: 11/584,556

(22) Filed: Oct. 23, 2006

(65) Prior Publication Data

US 2009/0012162 A1 Jan. 8, 2009

Related U.S. Application Data

(63) Continuation of application No. PCT/FR2005/001008, filed on Apr. 22, 2005.

(30) Foreign Application Priority Data

Apr. 23, 2004 (FR) ..................... 04 04344

(51) Int. Cl.
*A61P 29/00* (2006.01)
*A61K 31/231* (2006.01)
*A61K 31/045* (2006.01)
*A61K 31/122* (2006.01)
*A61K 31/015* (2006.01)
*A61K 31/22* (2006.01)
*C11B 9/00* (2006.01)

(52) U.S. Cl.
CPC ............. *A61K 31/015* (2013.01); *A61K 31/045* (2013.01); *A61K 31/22* (2013.01); *A61K 31/122* (2013.01)
USPC ........... 514/546; 514/526; 514/690; 514/739; 514/763; 426/651

(58) Field of Classification Search
None
See application file for complete search history.

(56) References Cited

U.S. PATENT DOCUMENTS

| 5,599,546 A | 2/1997 | Klein |
| 6,177,472 B1 | 1/2001 | Wilson et al. |
| 2003/0104089 A1 | 6/2003 | Lee |
| 2003/0199592 A1 | 10/2003 | Wilkins |
| 2006/0241130 A1* | 10/2006 | Keinan et al. ............ 514/263.31 |

FOREIGN PATENT DOCUMENTS

| DE | 19644422 A1 | 4/1998 |
| DE | 199 15 102 A1 | 10/2000 |
| FR | 2 671 721 A | 7/1992 |
| JP | 4334319 A | 11/1992 |
| JP | 11-035455 A | 2/1999 |
| JP | 2004-002237 A | 1/2004 |
| KR | 20010066473 A | 9/2001 |
| WO | WO-99/35116 A1 | 7/1999 |
| WO | WO-01/78706 A | 10/2001 |
| WO | WO-02/13840 A | 2/2002 |

OTHER PUBLICATIONS

"Osteoarthritis of the Knee: An Information Booklet", Apr. 2005, available at www.arc.org.uk/arthinfo/patpubs/6027/6027.asp, 14 pages as printed.*
Bisson et al (2008. Rejuvenation Research. 11(2): 399-407).*
Tsirpanlis (2008, Am J Kidney Dis. 51: 131-144).*
Foreman et al (2003. Experimental Gerontology. 38: 1251-1257).*
Chen et al (2006. Cardiovascular & Haematological Disorders—Drug Targets. 6: 279-304).*
Bonnet et al (2004. Rheumatology. 44: 7-16).*
Lavigne et al (2005. Expert Opin Biol Ther. 5(3): 313-320).*
Hung et al (2008. European Journal of Pharmacology. 586: 275-282).*
Ikeda et al, 2008. Mol Nutr Food Res. 52: 26-42).*
Souza et al, 2003. Pharmazie. 58: 582-586.*
Limonene, WS263303 Specification Sheet, Sigma-Aldrich, 2009, 1 page as printed.*
Gershenzon et al (2007. Nature Chemical Biology. 3(7): 408-414).*
English translation made by machine on Dec. 2, 2013 of Lee et al, KR20010086473,published Sep. 12, 2001, 10 pages as printed.*
Stohs S J. Journal of Basic and Clinical Physiology and Pharmacology, Freund Publishing House Ltd., London, GB, vol. 6, No. 3/4, 1995, pp. 205-228.

* cited by examiner

*Primary Examiner* — Zachary Howard
(74) *Attorney, Agent, or Firm* — Birch, Stewart, Kolasch & Birch, LLP

(57) ABSTRACT

The invention relates to the use of a molecule selected from the group which consists of geranyl acetate, geraniol, isomenthone, limonene or a mixture of at least two of the above, for preparing a drug for treating or preventing vascular endothelial cell senescence and subjacent tissue degeneration induced by repeated inflammatory episodes. Specifically, the drug is useful for treating vascular endothelial cell senescence and tissue degeneration induced by repeated inflammatory episodes resulting from the presence of cancer cells.

11 Claims, 27 Drawing Sheets

WBC Value range: 1.8-10.2 according to Jackson Laboratories

RBC Value range: 9-10.2
according to Jackson Laboratories

HGB Value range: 13.5-15.6
according to Jackson Laboratories

HCT Value range: 44.1-48.4
according to Jackson Laboratories

PLT Value range: 1,178-1,374 according to Jackson Laboratories

|  | Avg. | S.D. |
|---|---|---|
| Dose 5µg | 8.65 | 1.77 |
| Dose 10µg | 10.65 | 0.3 |
| Dose 20µg | 9.53 | 1.41 |
| Control Avg. | 8.44 | 0.38 |

**WBC Value range: 1.8-10.2
according to Jackson Laboratories**

|  | Avg. | S.D. |
|---|---|---|
| Dose 5µg | 8.91 | 0.52 |
| Dose 10µg | 9.48 | 0.58 |
| Dose 20µg | 7.92 | 1.00 |

**RBC Value range: 9-10.2
according to Jackson Laboratories**

|           | Avg.    | S.D. |
|-----------|---------|------|
| Dose 5µg  | 14.32   | 0.61 |
| Dose 10µg | 14.55   | 0.56 |
| Dose 20µg | 13.325  | 1.60 |

**HGB Value range: 13.5-15.6
according to Jackson Laboratories**

|  | Avg. | S.D. |
|---|---|---|
| Dose 5µg | 39.12 | 1.20 |
| Dose 10µg | 40.5 | 1.61 |
| Dose 20µg | 36.02 | 3.25 |

HCT Value range: 44.1-48.4
according to Jackson Laboratories

|  | Avg. | S.D. |
|---|---|---|
| Dose 5µg | 1,107.8 | 122.43 |
| Dose 10µg | 967 | 171.84 |
| Dose 20µg | 1214.8 | 88.85 |
| Control Avg. | 1,159.75 | 127.33 |

PLT Value range: 1,178-1,374 according to Jackson Laboratories

METHOD FOR TREATING CELL DEGENERATION USING AT LEAST ONE MOLECULE CAPABLE OF INHIBITING ADHESION MOLECULE EXPRESSION AND VASCULAR ENDOTHELIUM ACTIN FIBRE POLYMERIZATION

This application is a Continuation of copending PCT International Application No. PCT/FR2005/001008 filed on Apr. 22, 2005, which designated the United States, and on which priority is claimed under 35 U.S.C. §120. This application also claims priority under 35 U.S.C. §119(a) on Patent Application No(s). 0404344 filed in France on Apr. 23, 2004. The entire contents of each of the above documents is hereby incorporated by reference.

FIELD OF THE INVENTION

This invention relates to the study of the reversion of tissue senescence mediated by vascular endothelium cells. More particularly, this invention relates to the effects of plant-origin compounds of terpene type on the vascular endothelium during inflammatory episodes. Such compounds are capable of inhibiting the expression of endothelial adhesion molecules and the polymerisation of endothelial actin fibres during inflammatory episodes. This inhibition protects the sub-epithelial tissues from the toxic effects of inflammation which accelerate their degeneration.

BACKGROUND OF THE INVENTION

Indeed, the senescence of the vascular endothelium and the degeneration of the tissues subjected to inflammatory processes are accelerated by repeated or chronic inflammation of the vascular endothelium.

Cell senescence is a phenomenon resulting in an increase in the volume of the cell, a decrease in or loss of the normal capacity of the cell to divide, a decrease in its regenerative and metabolic functions, and an increase in the activity of cellular degradative enzymes. All these changes characterize the senescent phenotype.

This senescent phenotype has been observed in young cells subjected to repeated stress due to inflammatory reactions.

The initial phase of inflammation occurs at the blood/tissue interface and consists in the recruitment of immunologically competent cells, in particular activated leucocytes. Inflammation consists in targeting and killing infectious microorganisms and other pathogens. The immunologically competent cells capable of acting against these microorganisms circulate in blood and must therefore enter the tissues to carry out their role; to do this, they must cross the barrier formed by the vascular wall. They do this by being recruited by the vascular endothelial cells lining the vessels and which transfer them into the underlying tissue. Vascular endothelial cells are activated by specific signals from infected or injured tissue, or directly by the immunologically competent cells, and this activation results in the effect of a significant increase of their recruitment ability. The state of activation of vascular endothelial cells can be measured by the appearance of specific markers. In particular, the expression level of adhesion molecules such as ICAM-1 (INTER-CELLULAR ADHESION MOLECULE-1) allows the degree of vascular endothelial cells activation leading to the recruitment of immunologically competent cells to be assessed.

Another consequence of inflammatory stress is the rearrangement of the actin cytoskeleton in activated vascular endothelial cells. Inflammatory stress results in the formation of polymerised actin fibres (so-called "stress" fibres) that can be revealed by rhodamine-conjugated phalloidin staining.

Under normal circumstances, in a primary cell culture of vascular endothelial cells, the activation due to an inflammatory state of the cells is reversible. During senescence, cells gradually lose this reversibility and thus permanently express adhesion molecules, even in the absence of an external stimulation. There are two consequences for this loss of reversibility: firstly, the constant recruitment of immunologically competent cells is an additional source of inflammatory stress for tissues; and secondly, because of this, vascular endothelial cells are more available to recruit tumour metastases which use the same adhesion molecules to invade tissues.

SUMMARY OF THE INVENTION

Accordingly, this invention relates to the use of a molecule selected from the group consisting of geranyl acetate, geraniol, isomenthone, limonene, or a mixture of at least two of these, for the preparation of a drug for treating or preventing tissue degeneration associated with the senescence of vascular endothelial cells induced by repeated inflammatory episodes.

DETAILED DESCRIPTION OF THE PREFERRED EMBODIMENTS

These molecules have in common their capacity to inhibit the irreversible activation of vascular endothelial cells, and to maintain these cells in a state of functional activation in which they are capable of responding to an environmental stimulation and then return to their baseline state. These molecules are capable of reversing the senescent phenotype of a vascular endothelial cell when it has already been detected, and they are thus cytoprotective, because they protect the cells of underlying tissues from the inflammatory effectors secreted by the activated immunologically competent cells, thus preventing their degeneration. The use according to this invention involves at least one molecule having this capacity.

These molecules are contained in or derived from essential oils of plant origin. Advantageously, they are isolated and purified or are prepared by chemical synthesis.

Geranyl acetate is (E)-3,7-dimethyl-2,6-octadienyl acetate (CAS No. 105-87-3). It is present in the essential oils of rose, lemon balm, lemon grass, geranium and orange blossom (neroli oil), amongst others.

Geraniol is (E)-3,7-dimethyl-2,6-octadien-1-ol (CAS No. 106-24-1). It is present in the essential oils of rose, orange blossom (neroli oil) and geranium, amongst others.

Isomenthone is cis-2-isopropyl-5-methylcyclohexanone (CAS No. 491-07-6), present in the essential oils of mint and geranium, amongst others.

Limonene is (4R)-1-methyl-4-isopropenylcyclohex-1-ene (CAS No. 5989-27-5). It is present in the essential oils of lemon and orange blossom (neroli oil), amongst others.

Advantageously, these molecules are used according to the invention in a composition in which they are present in very small amounts.

According to a first embodiment, the invention relates to the senescence of vascular endothelial cells induced by repeated inflammatory episodes resulting from the presence of cancer cells. Accordingly, the invention relates to the preparation of a drug for treating the spread of metastases promoted by an overexpression of adhesion molecules by the vascular endothelium and a polymerisation of vascular endothelial actin, two phenomena which are responsible for the recruitment of potentially metastatic cancer cells.

According to a second embodiment, the invention relates to the senescence of vascular endothelial cells and secondarily to the tissue degeneration induced by repeated inflammatory episodes resulting from exposure to the sun (UV), pollution, or micro-abrasions. Accordingly, the invention relates to the preparation of a drug for treating dermatological conditions and cutaneous allergies linked to the above phenomena which result in an overexpression of adhesion molecules by the vascular endothelium and a polymerisation of vascular endothelial actin, two phenomena which are associated with inflammatory episodes inducing degeneration of dermal tissues. According to the invention, said drug is useful for treating the senescence of dermal microvascular endothelial cells as well as tissue degeneration induced by repeated inflammatory episodes resulting from exposure to the sun (UV), pollution, or micro-abrasion.

According to a third embodiment, the invention relates to the senescence of vascular endothelial cells and secondarily to the degeneration of underlying tissues induced by repeated inflammatory episodes associated with chronic inflammatory or auto-immune diseases. Accordingly, the invention relates to the preparation of a drug for treating chronic inflammatory or auto-immune pathologies which result in an overexpression of adhesion molecules by the vascular endothelium and a polymerisation of vascular endothelial actin, and which induce degeneration of underlying tissue.

A chronic inflammatory or auto-immune pathology is chosen from the group consisting of rheumatoid arthritis, osteoarthritis, spondylarthritis, gout, arthrosis and any other form of arthritis, chronic hepatitis, ulcerative colitis, Crohn's disease, vasculitis, multiple sclerosis, psoriasis, systemic and cutaneous lupus erythematosus, and scleroderma.

According to a fourth embodiment, the invention relates to the senescence of vascular endothelial cells and secondarily to the tissues degeneration induced by repeated inflammatory episodes associated with degenerative diseases. Accordingly, the invention relates to the preparation of a drug for treating degenerative brain diseases associated with an overexpression of adhesion molecules by the vascular endothelium and a polymerisation of vascular endothelial actin, two phenomena which induce degeneration of cerebral tissue.

A degenerative brain pathology is chosen from the group consisting of Alzheimer's disease, vascular or mixed senile dementia, Parkinson's disease, and Huntington's disease.

Advantageously, the drug can be administered topically, orally, enterally, parenterally or through inhalation.

Other advantages and characteristics of the invention will become apparent in the following Examples concerning the inhibition of adhesion molecules and actin polymerisation of vascular endothelial cells under the action of geranyl acetate, geraniol, isomenthone or limonene. In these Examples, reference is made to the accompanying drawings, in which:

1/Geranyl acetate, FIGS. 1, 2, 3A, 3B

FIG. 1 shows the percentage of inhibition of ICAM-1 expression in HUVECs (Human Umbilical Vein Endothelial Cells) at different stages of replication (P1, P2 corresponding to young cell populations which have undergone a limited number of replication cycles, and P9 corresponding to cells which have reached their replication limit and are thus senescent), with 0.004% geranyl acetate following stimulation with TNF-α (Tumour Necrosis Factor-alpha) at a concentration of 10 ng/mL for 24 hours.

2/Geraniol, FIGS. 4, 5, 6A, 6B

Figure 1:
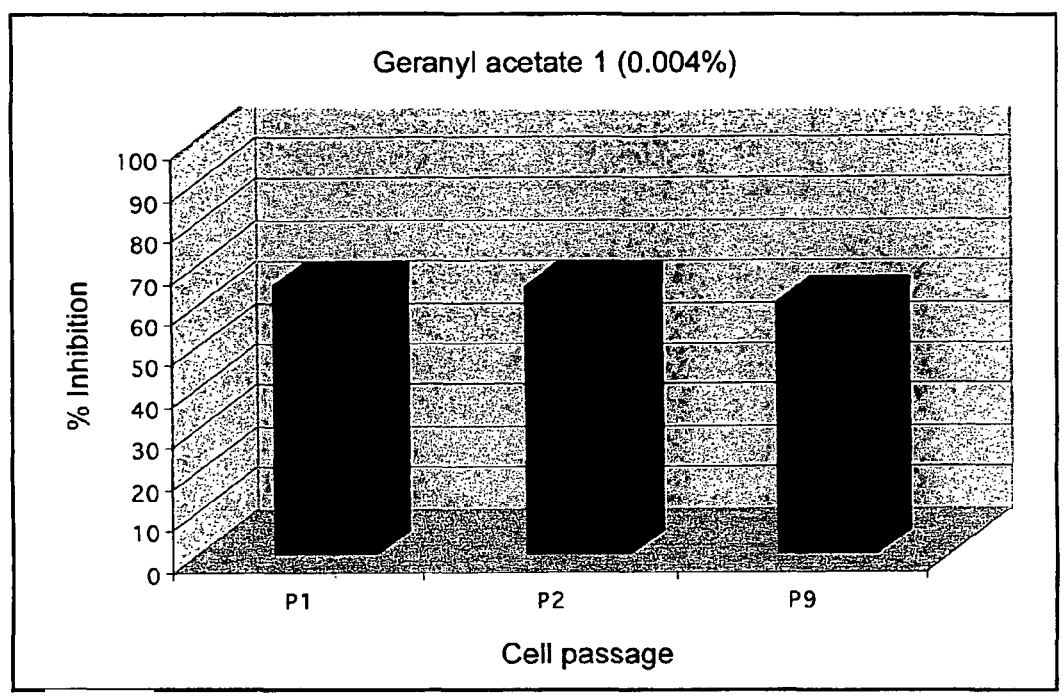
Figure 2:
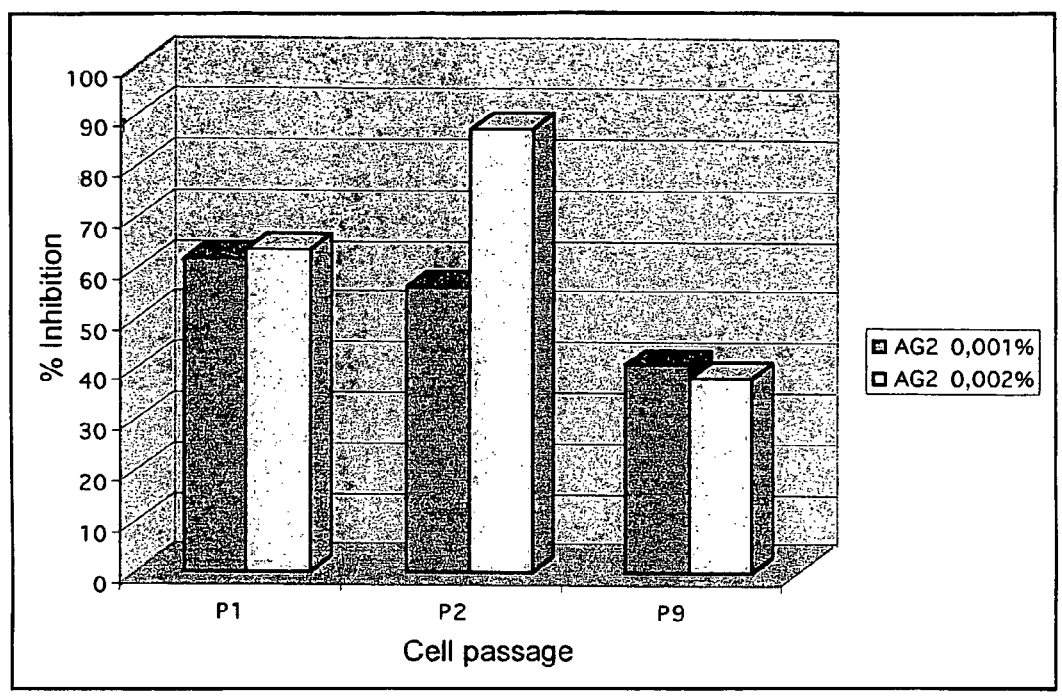
FIG. 2 shows the percentage of inhibition of ICAM-1 expression by HUVECs at different stages of replication with 0.001% or 0.002% geranyl acetate following stimulation with TNF-α at a concentration of 10 ng/mL for 24 hours.
Figure 3A:
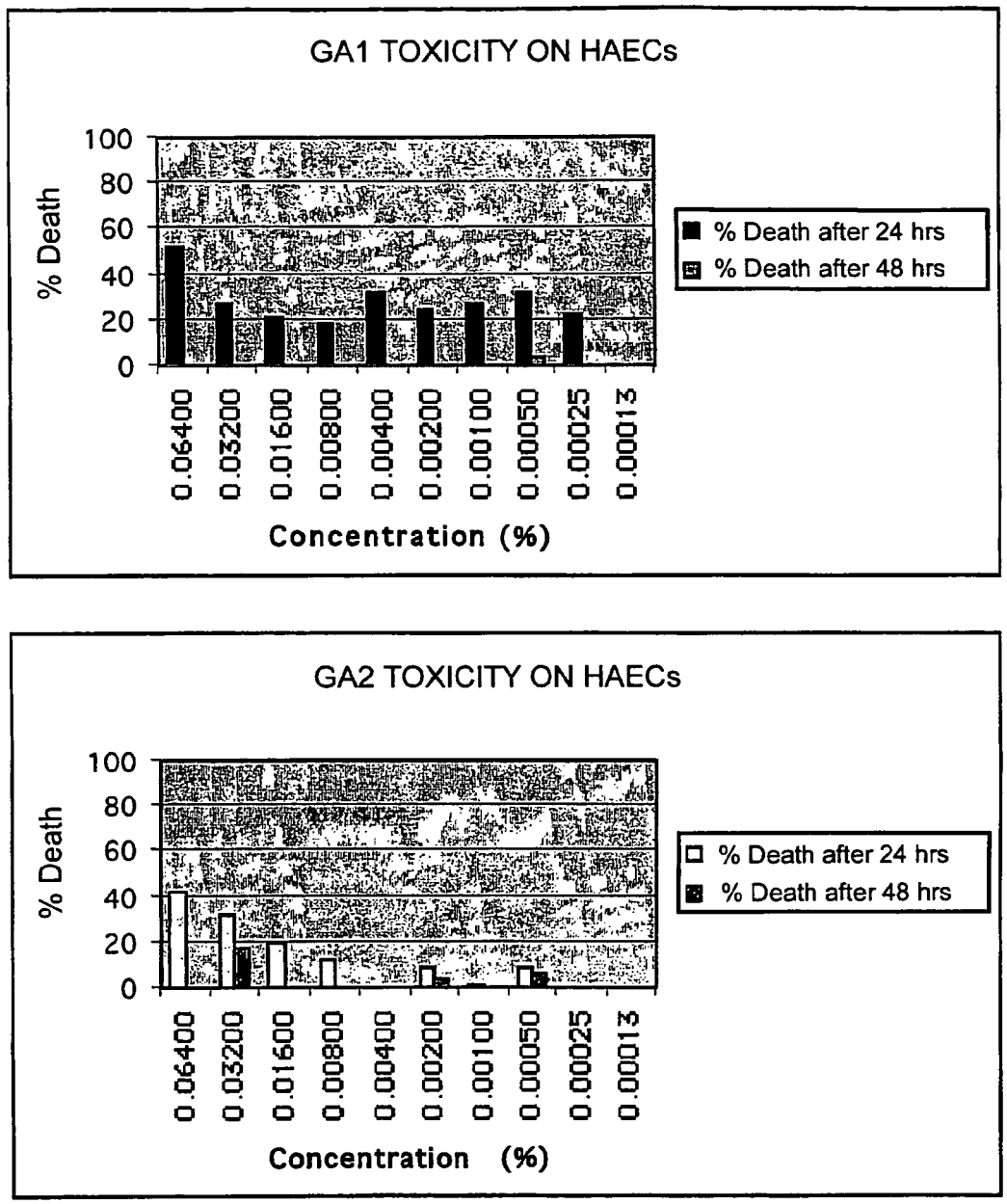
FIG. 3A shows the toxicity of geranyl acetate, as tested at different concentrations on HAECs (Human Aortic Endothelial Cells); the toxicity is given as the percentage of HAEC endothelial cells death after 24 and 48 hours.
Figure 3B:
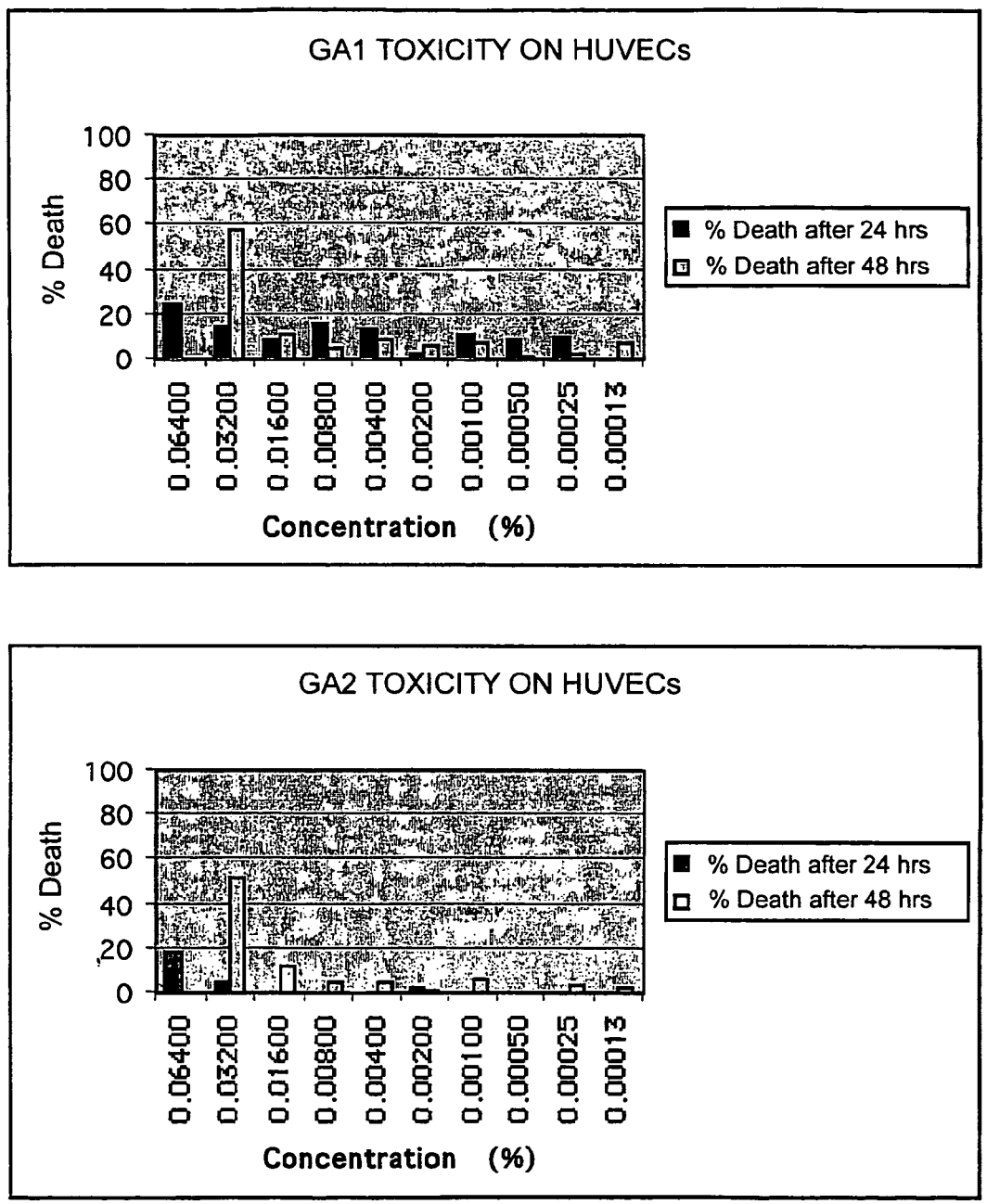
FIG. 3B shows the toxicity of geranyl acetate, as tested at different concentrations on HUVECs; the toxicity is given as the percentage of HUVEC endothelial cells death after 24 and 48 hours.
Figure 4:
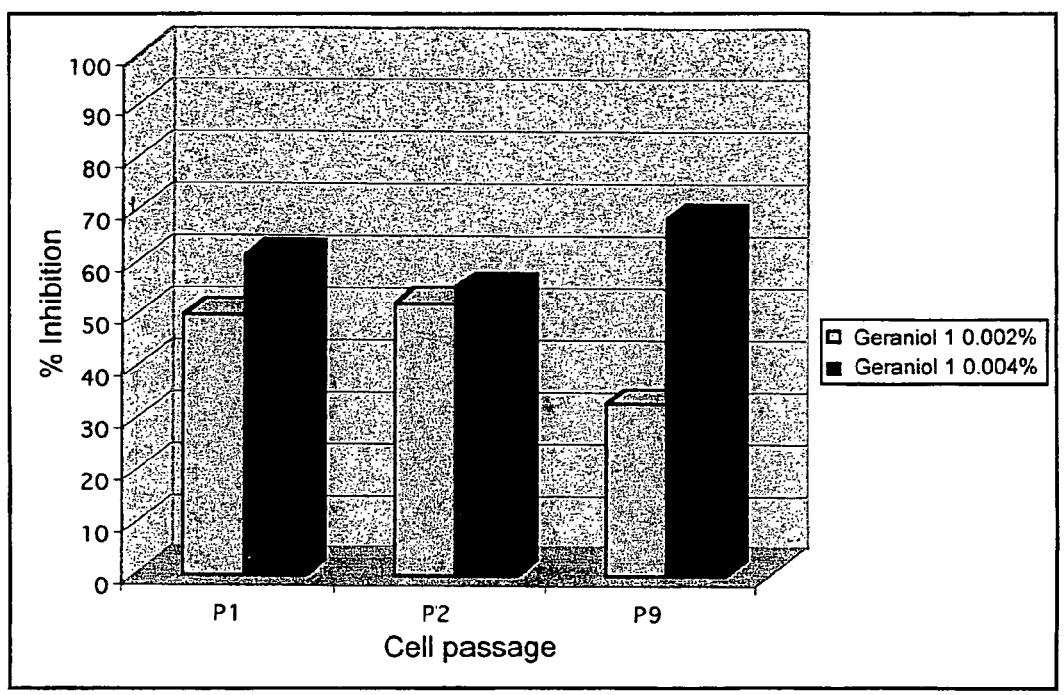

FIG. 4 shows the percentage of inhibition of ICAM-1 expression by HUVECS at different stages of replication with 0.002% and 0.004% geraniol following stimulation with TNF-α at a concentration of 10 ng/mL for 24 hours.

Figure 5:
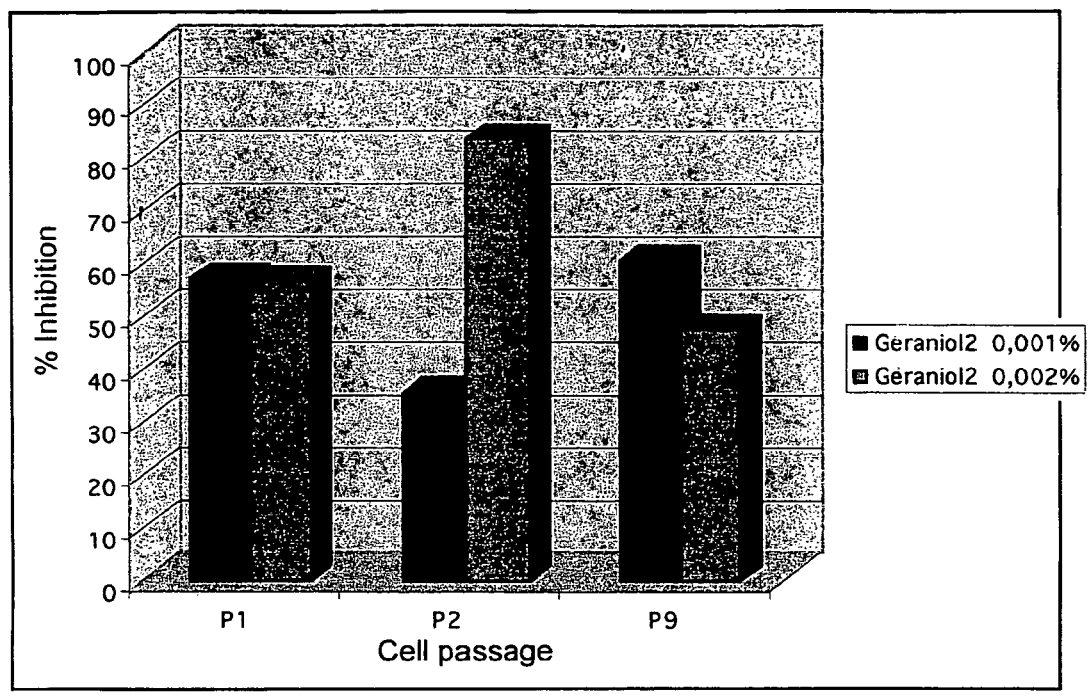

FIG. 5 shows the percentage of inhibition of ICAM-1 expression by HUVECs at different stages of replication with 0.001% and 0.002% geraniol following stimulation with TNF-α at a concentration of 10 ng/mL for 24 hours.

Figure 6A:
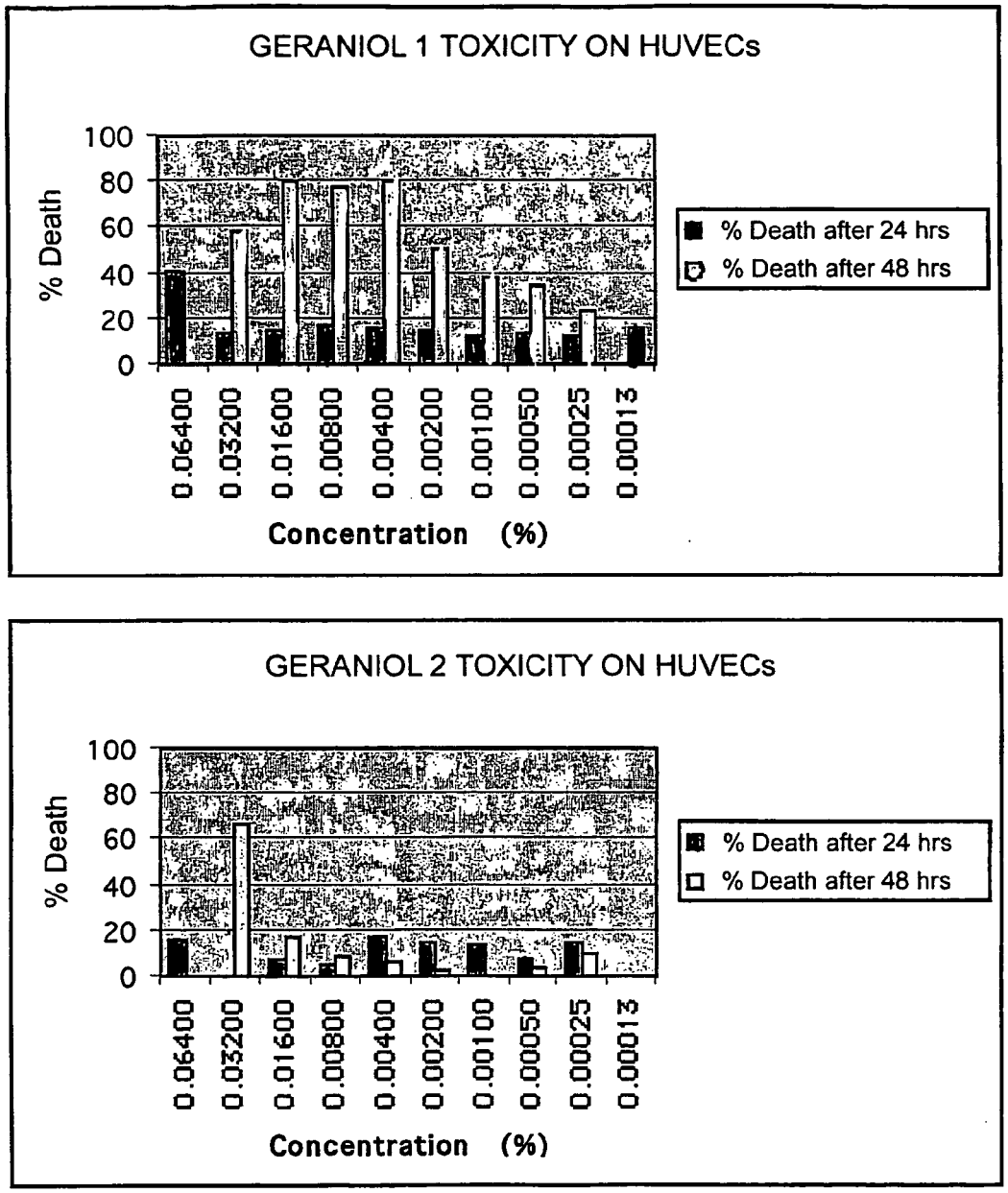

FIG. 6A shows the toxicity of geraniol, as tested at different concentrations on HUVECs; the toxicity is given as the percentage of HUVEC endothelial cells death after 24 and 48 hours.

Figure 6B:
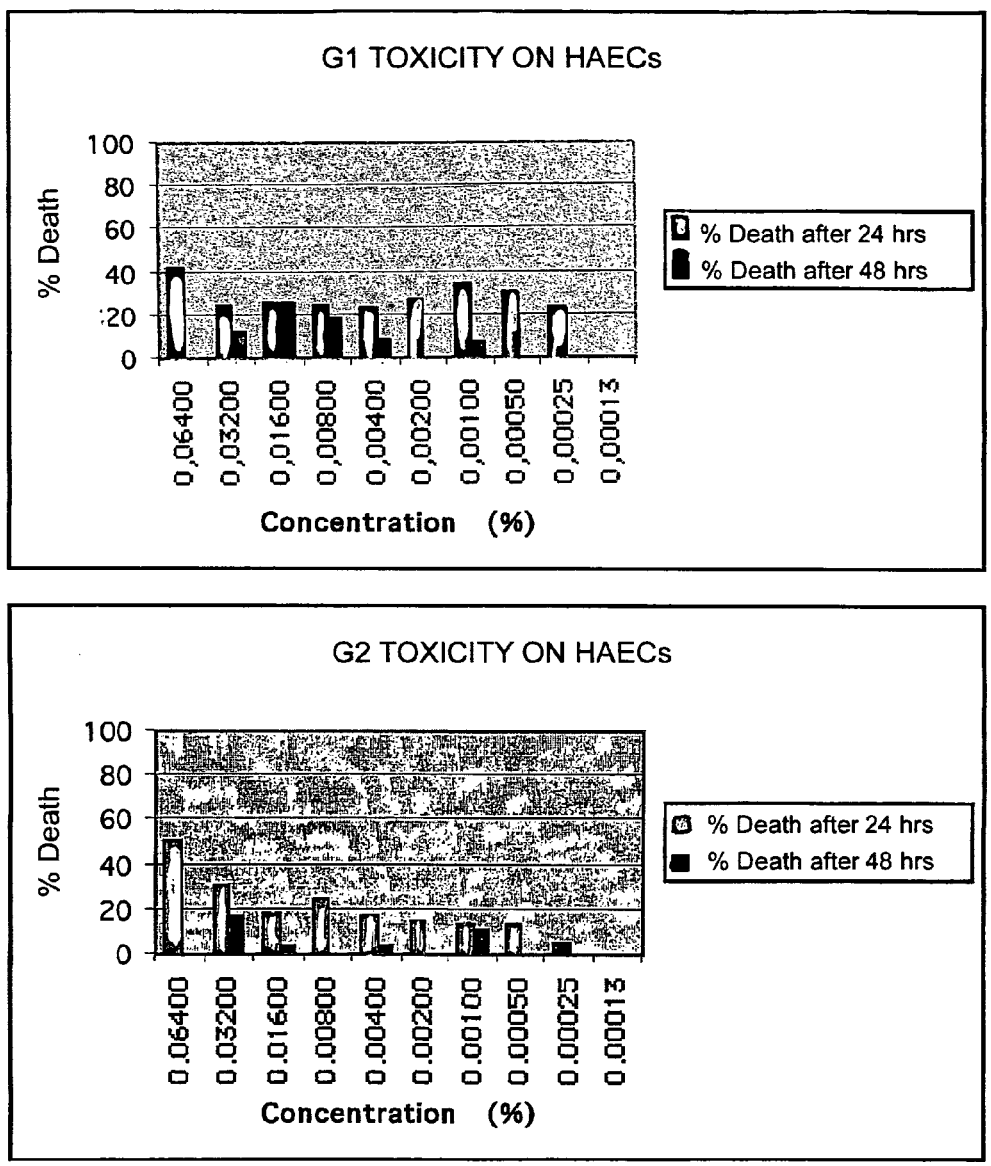

FIG. 6B shows the toxicity of geraniol, as tested at different concentrations on HAECs; the toxicity is given as the percentage of HAEC endothelial cells death after 24 and 48 hours.

Figure 7:
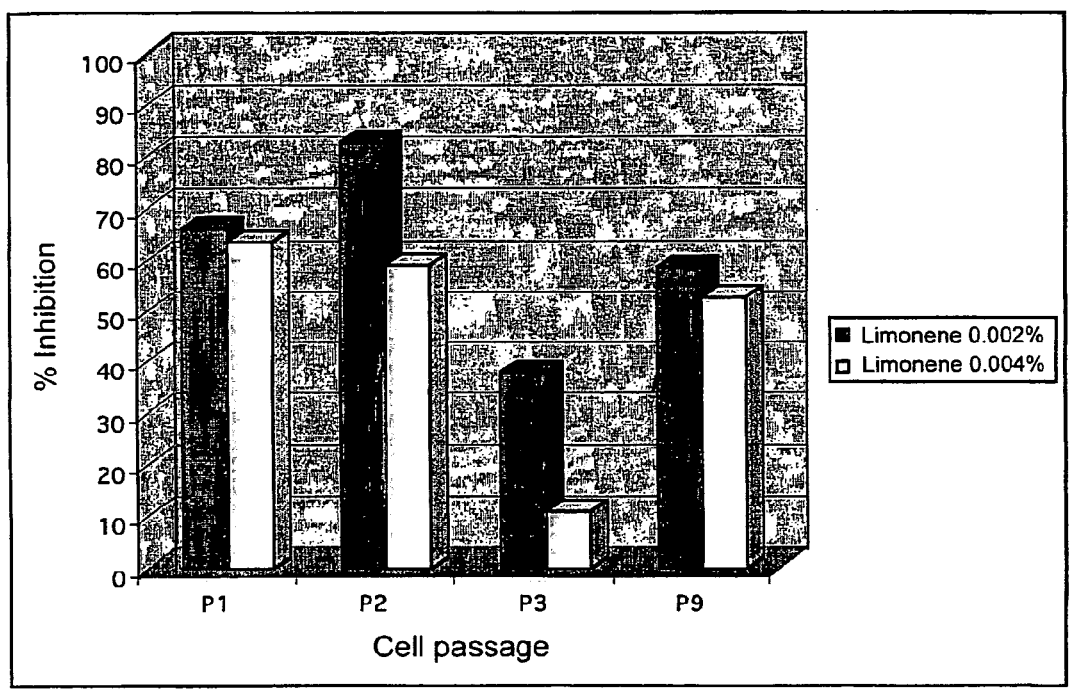
Figure 8A:
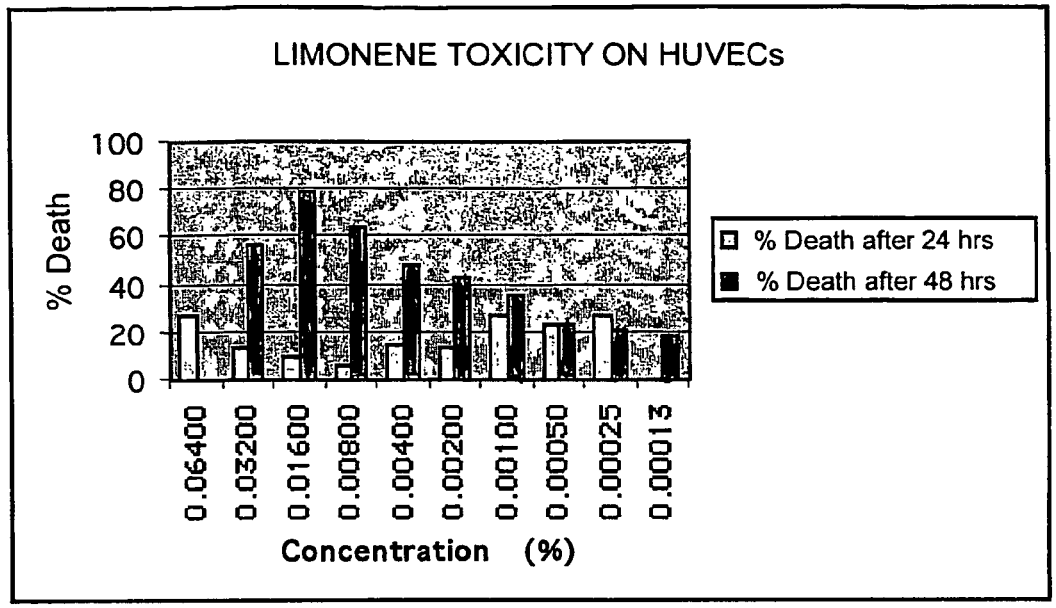
Figure 8B:
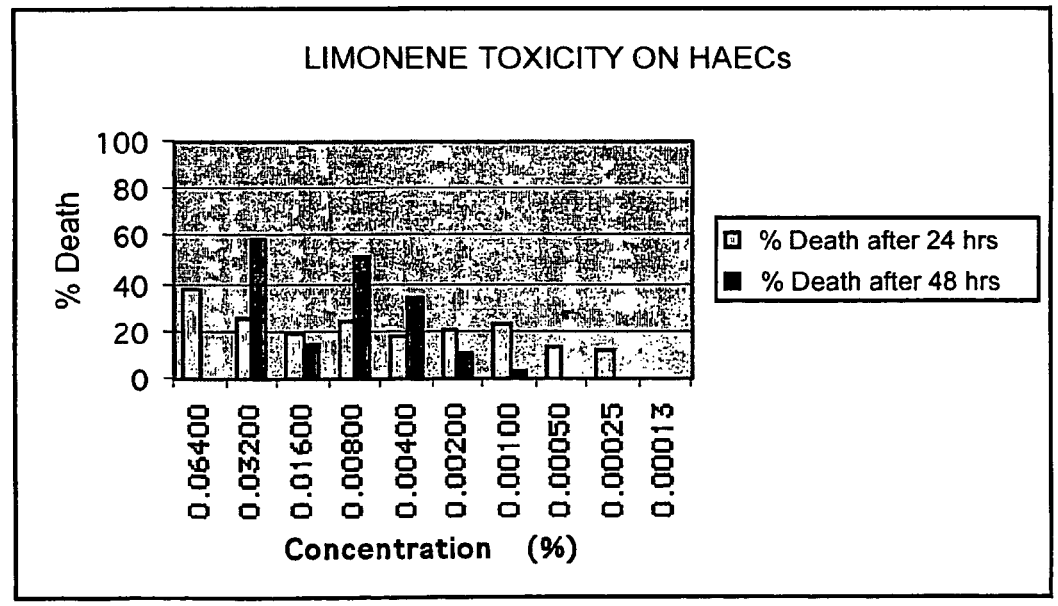

3/Limonene, FIGS. 7, 8A, 8B

FIG. 7 shows the percentage of inhibition of ICAM-1 expression by HUVECs at different stages of replication with 0.002% and 0.004% limonene following stimulation with TNF-α at a concentration of 10 ng/mL for 24 hours.

FIG. 8A shows the toxicity of limonene, as tested at different concentrations on HUVECs; the toxicity is given as the percentage of HUVEC endothelial cells death after 24 and 48 hours.

FIG. 8B shows the toxicity of limonene, as tested at different concentrations on HAECs; the toxicity is given as the percentage of HAEC endothelial cells death after 24 and 48 hours.

Figure 9:
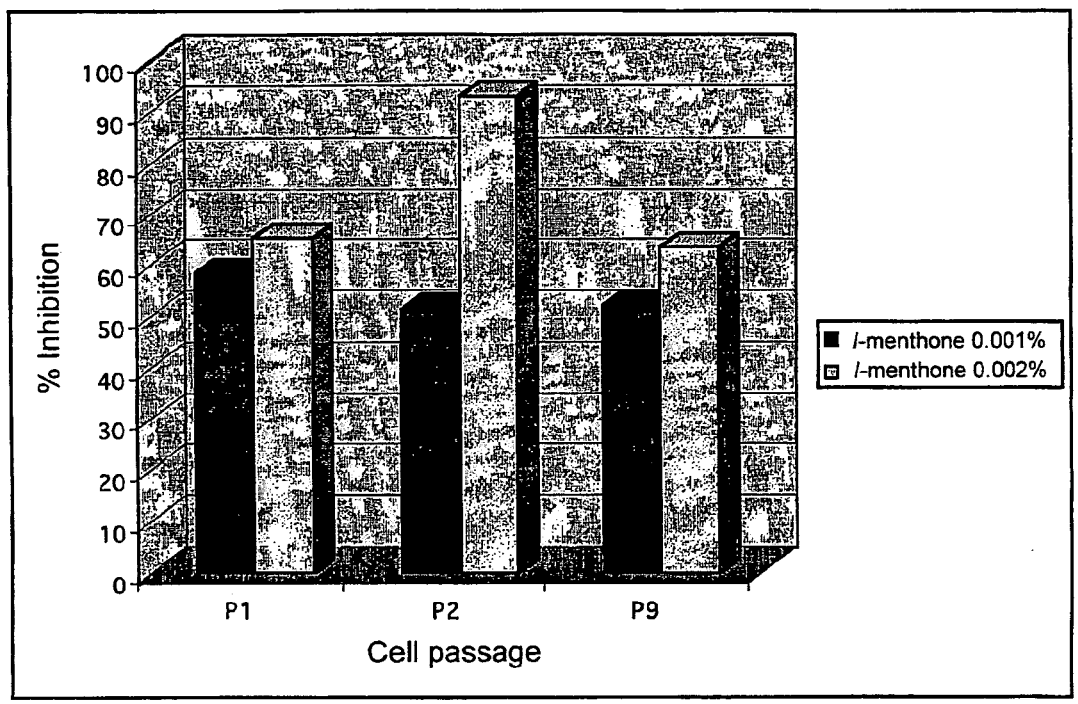
Figure 10A:
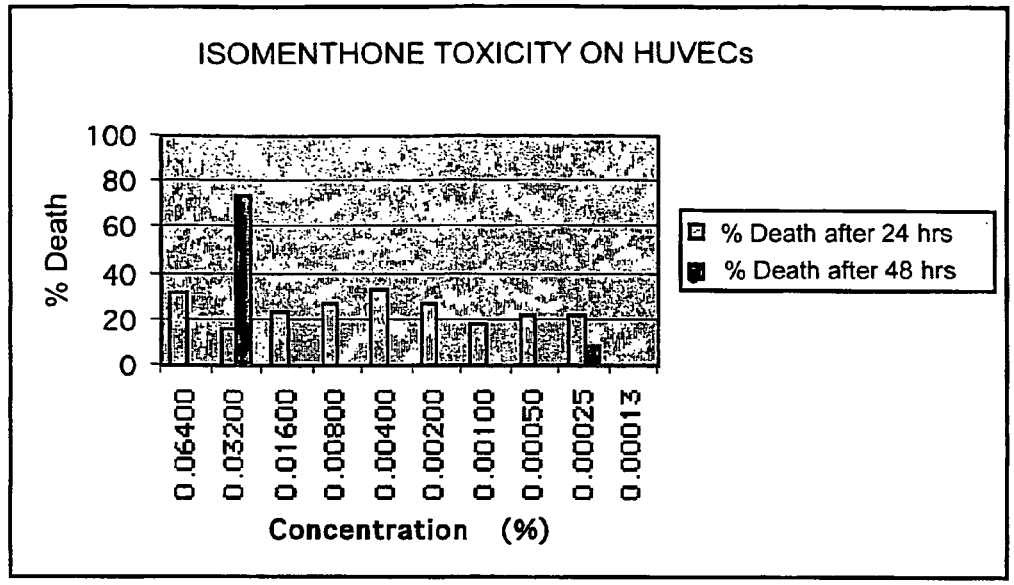
Figure 10B:
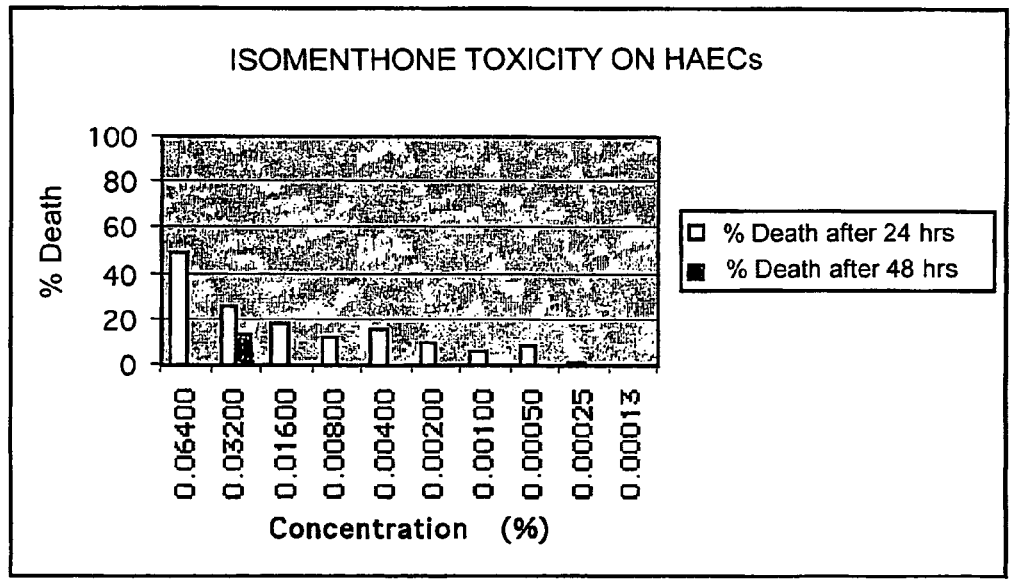
Figure 11:
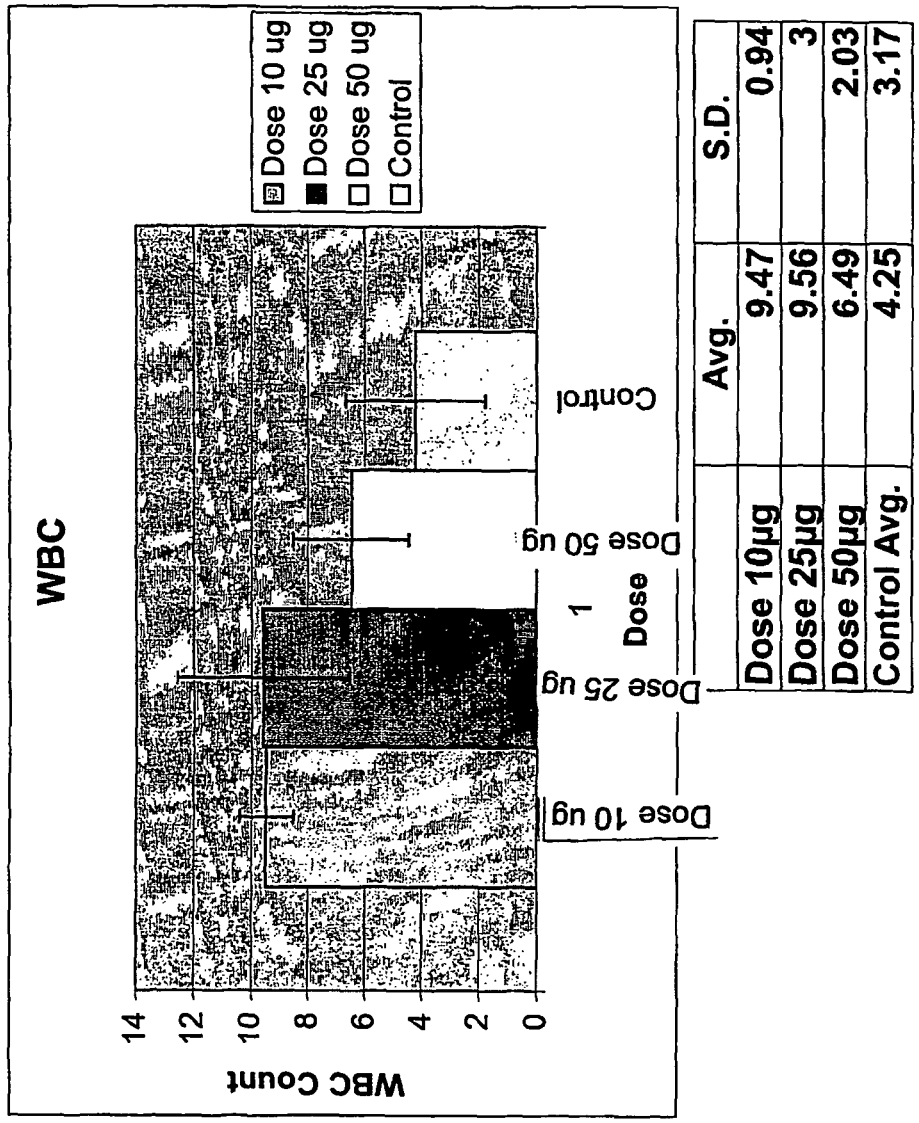
Figure 12:
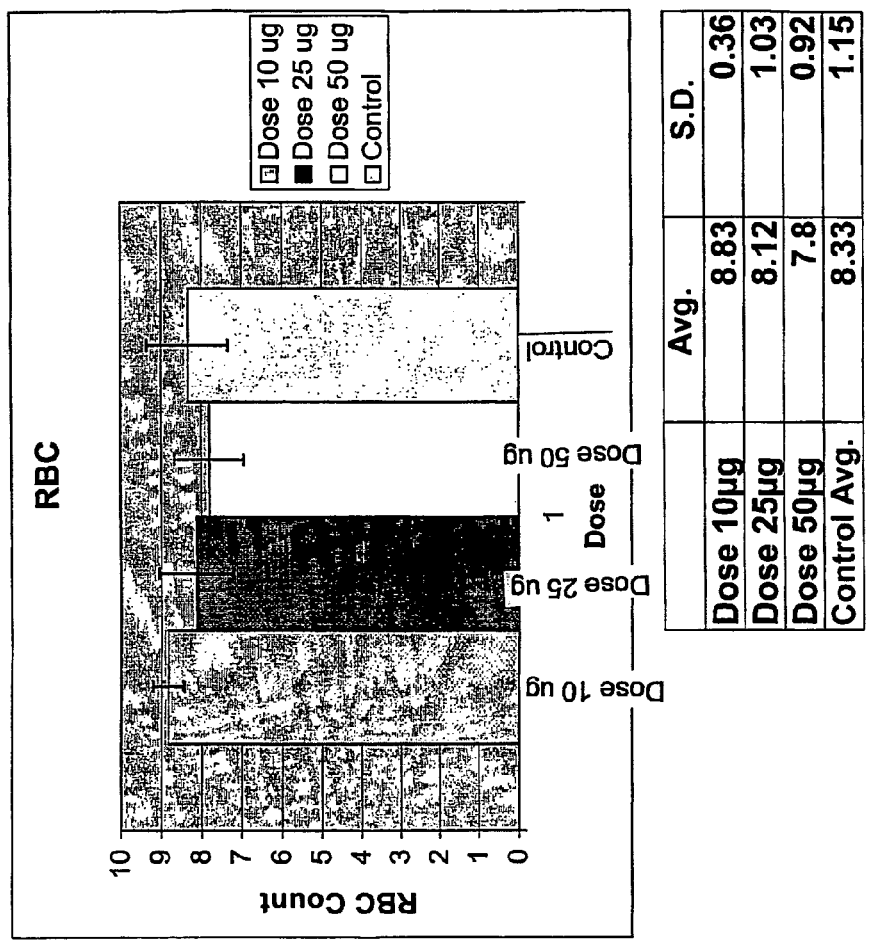
Figure 13:
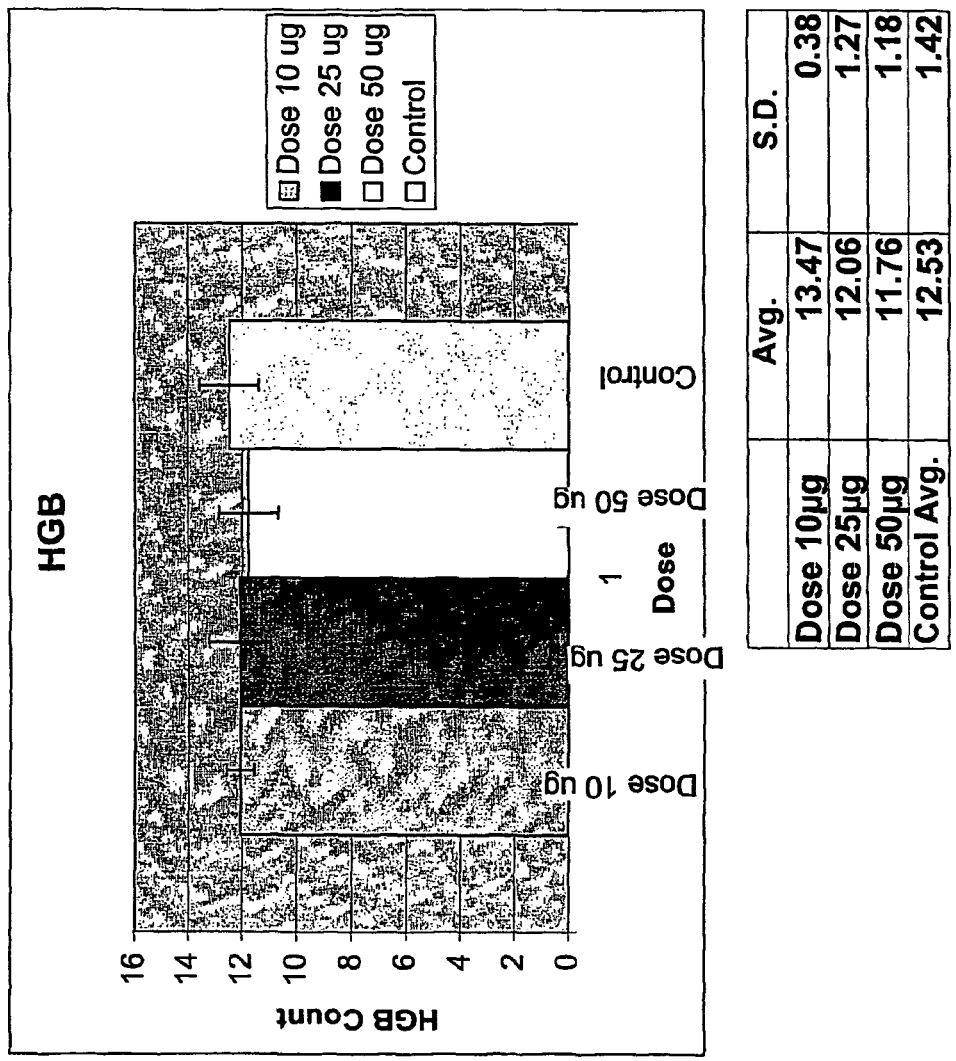
Figure 14:
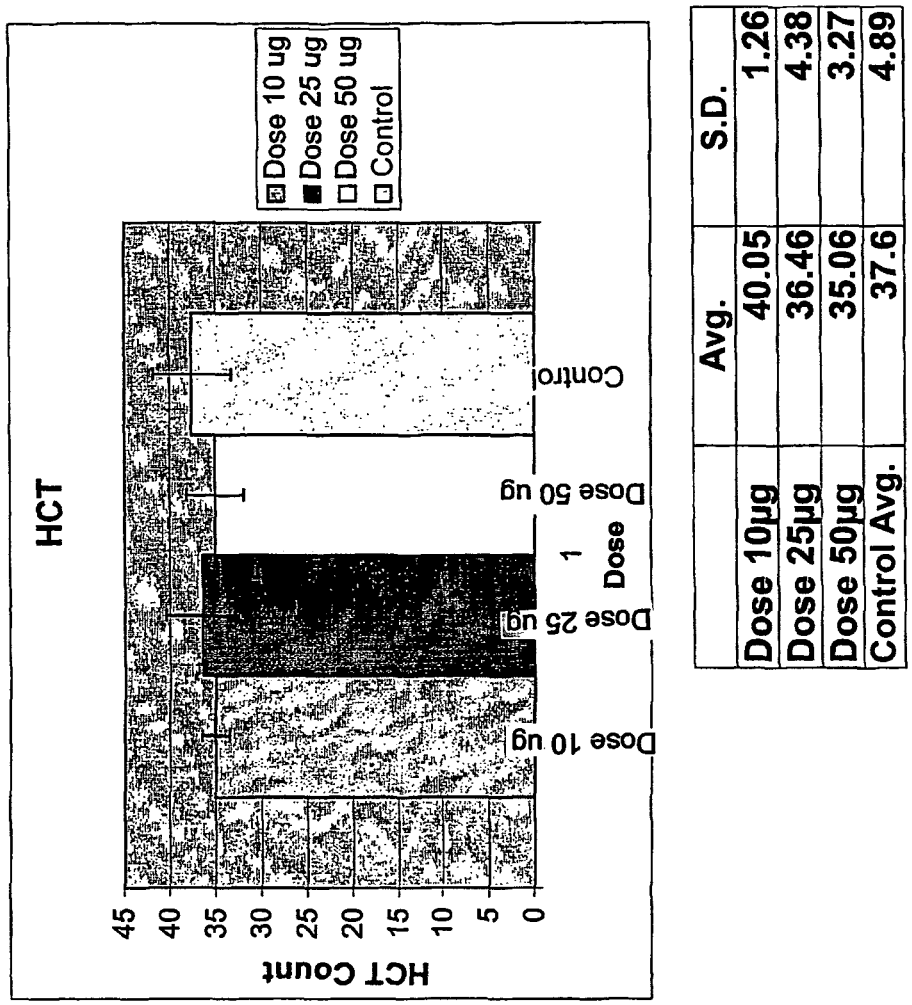
Figure 15:
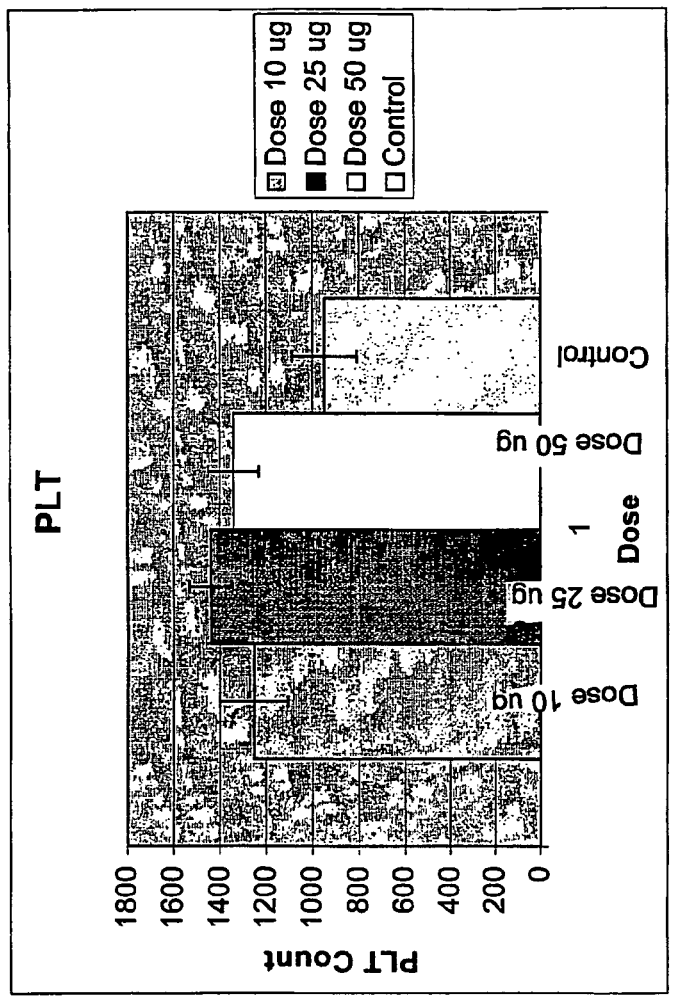
Figure 16:
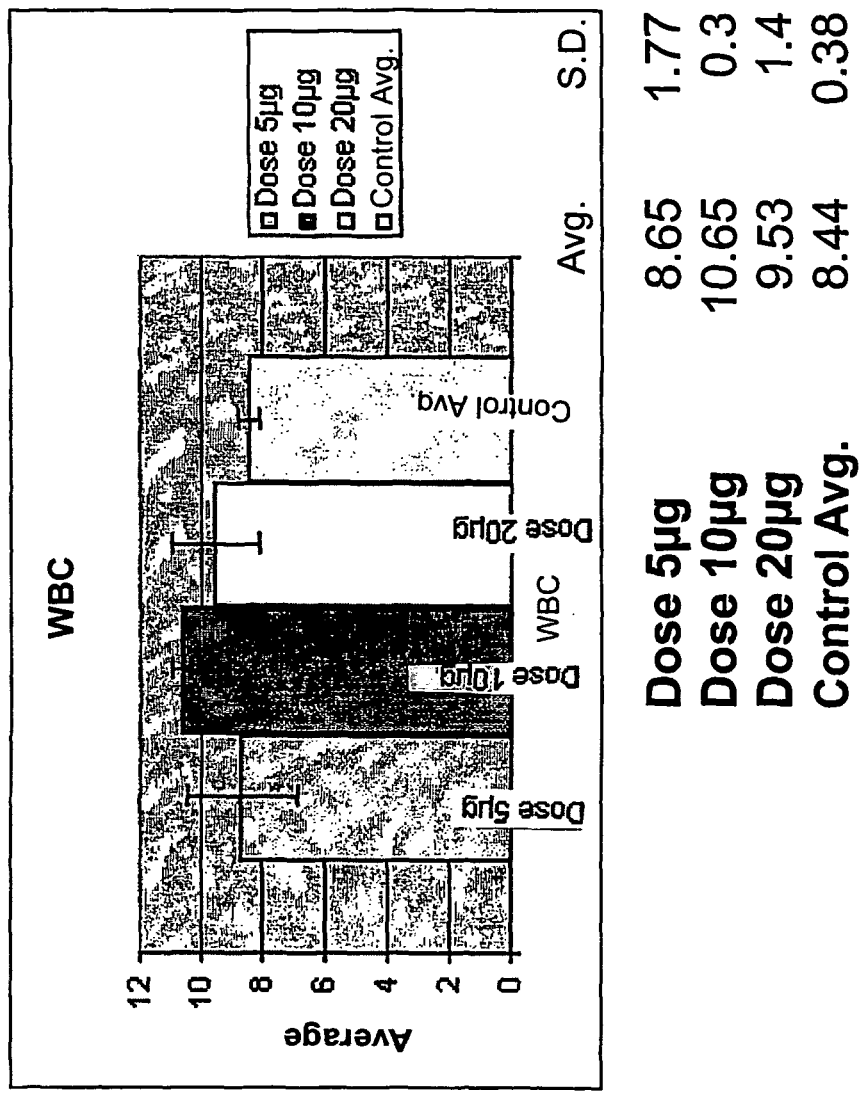
Figure 17:
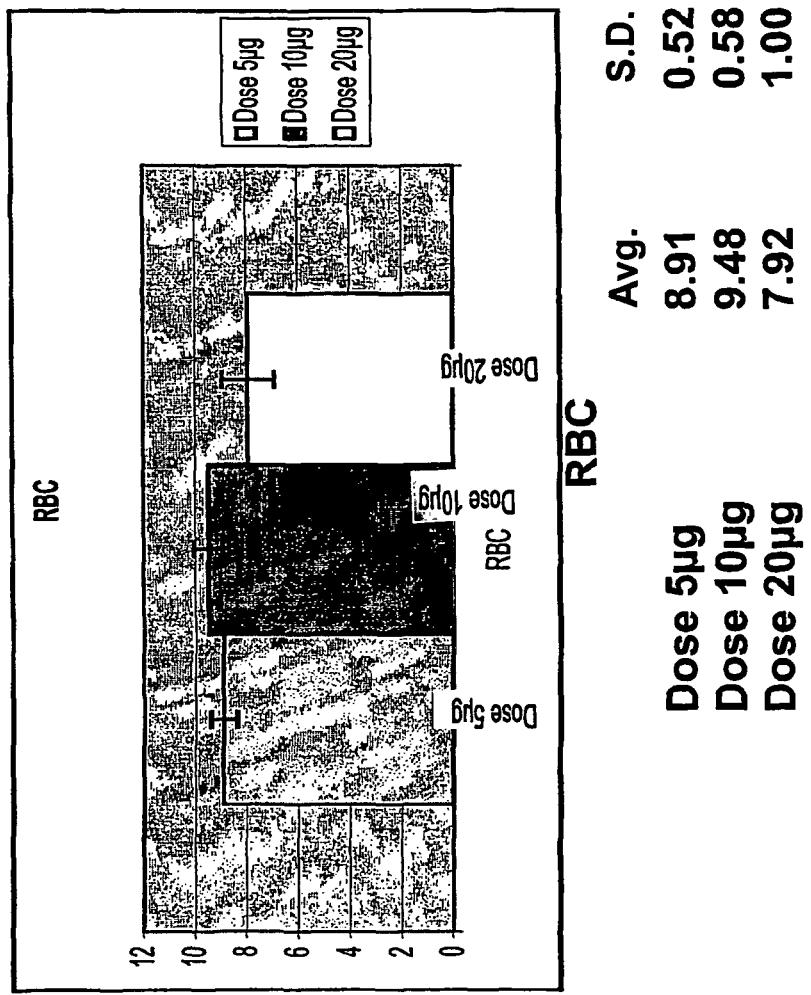
Figure 18:
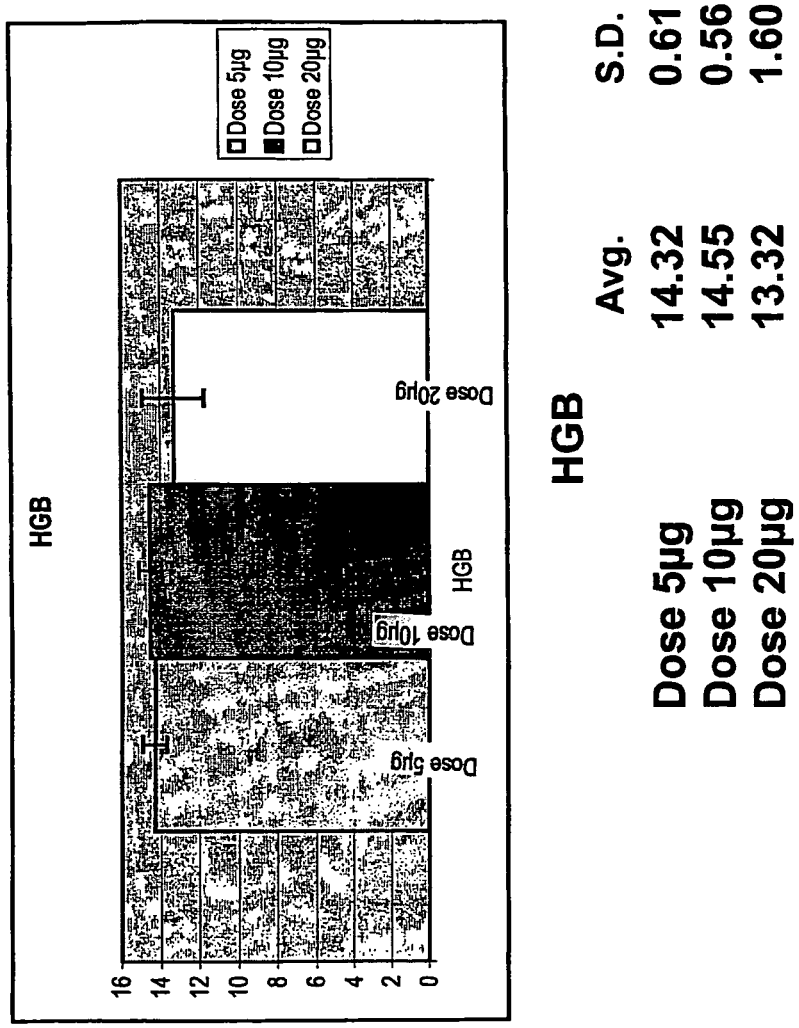
Figure 19:
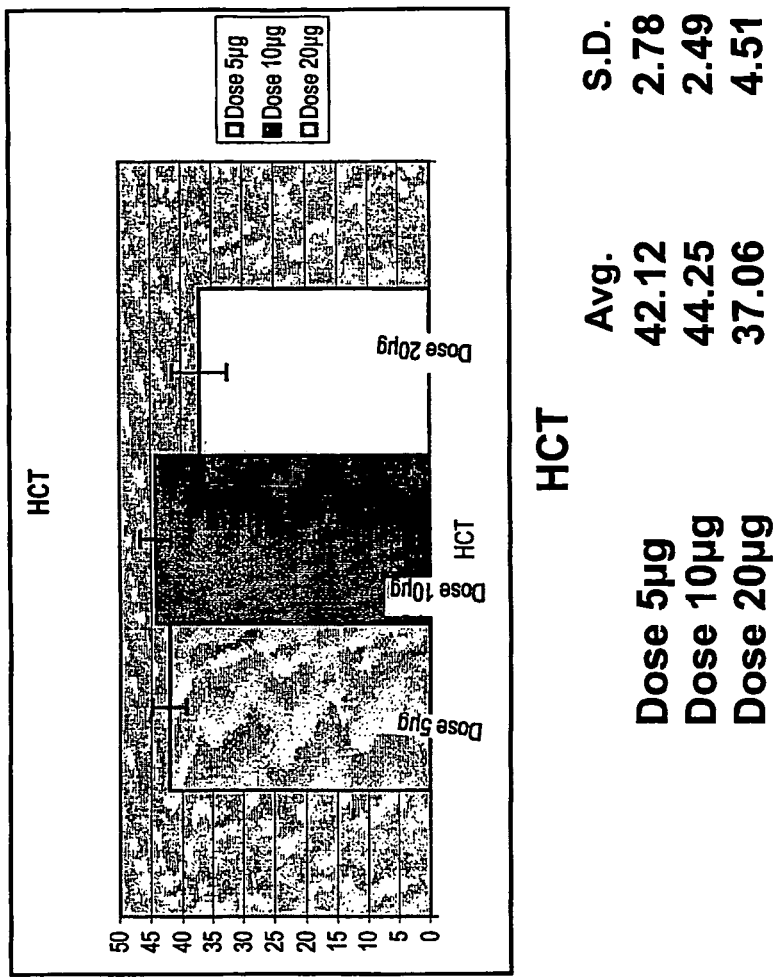
Figure 20:
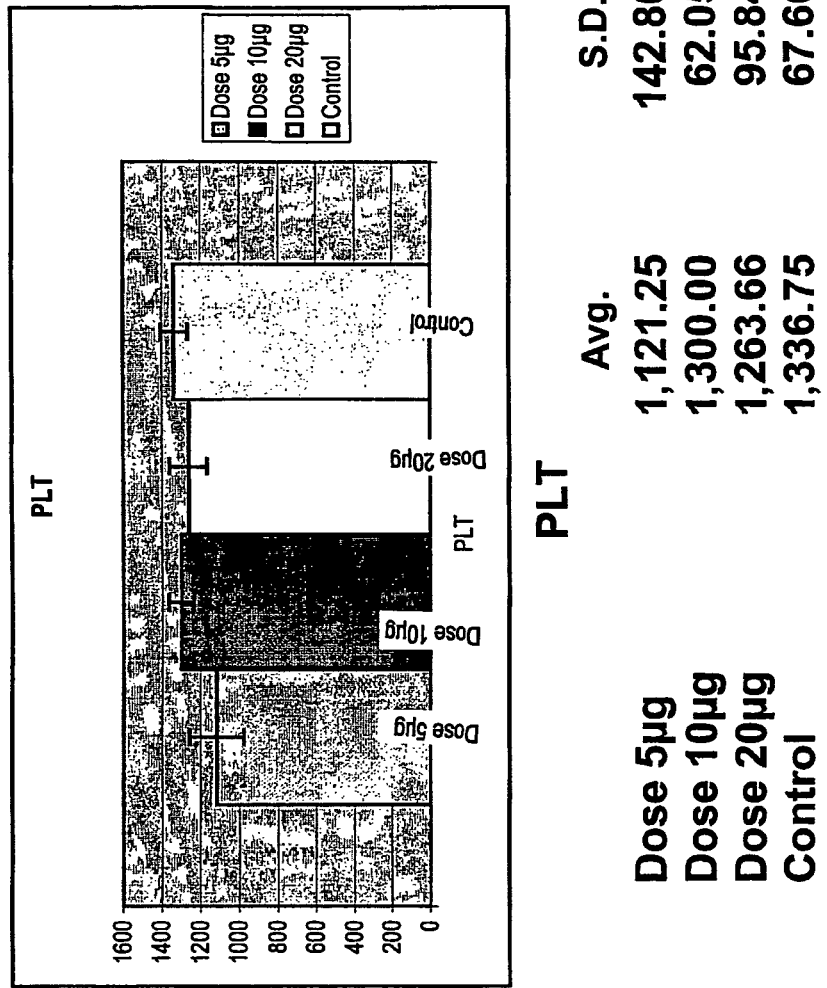
Figure 21:
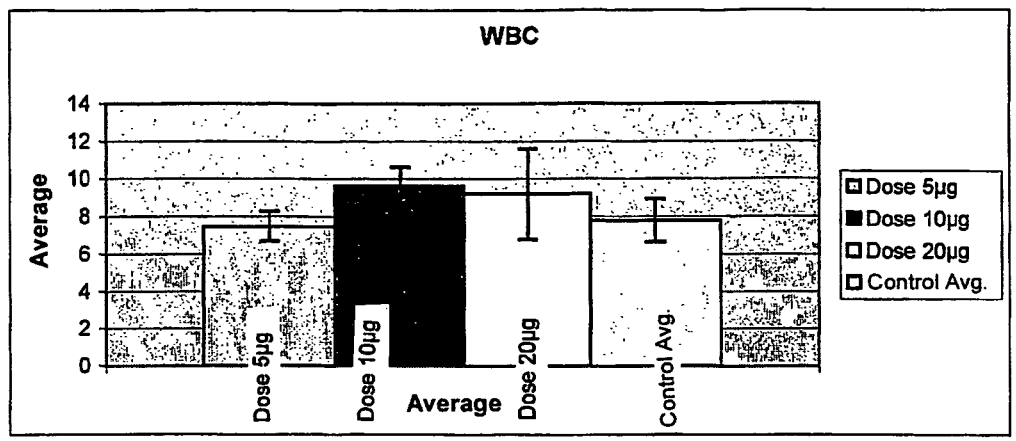
Figure 22:
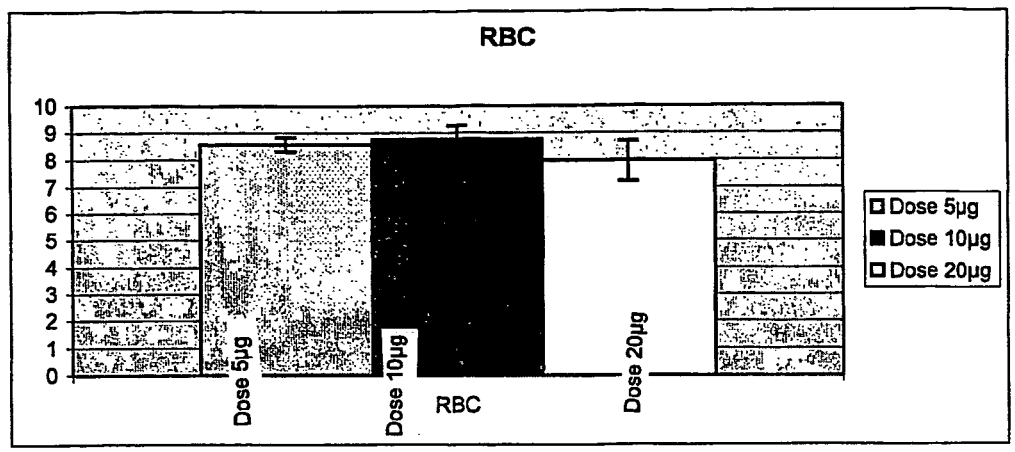
Figure 23:
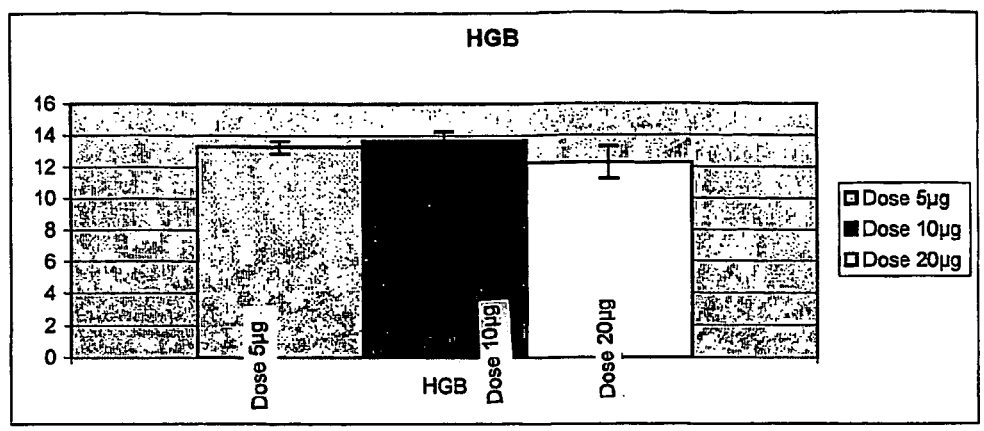
Figure 24:
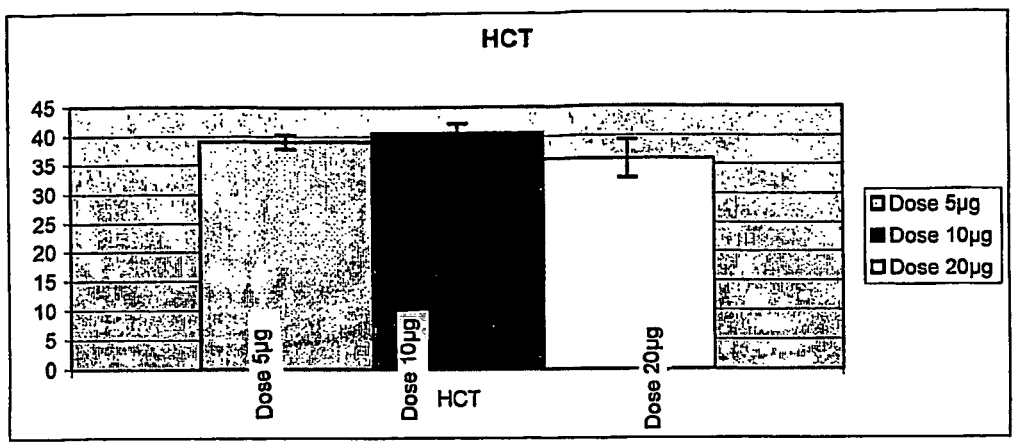
Figure 25:
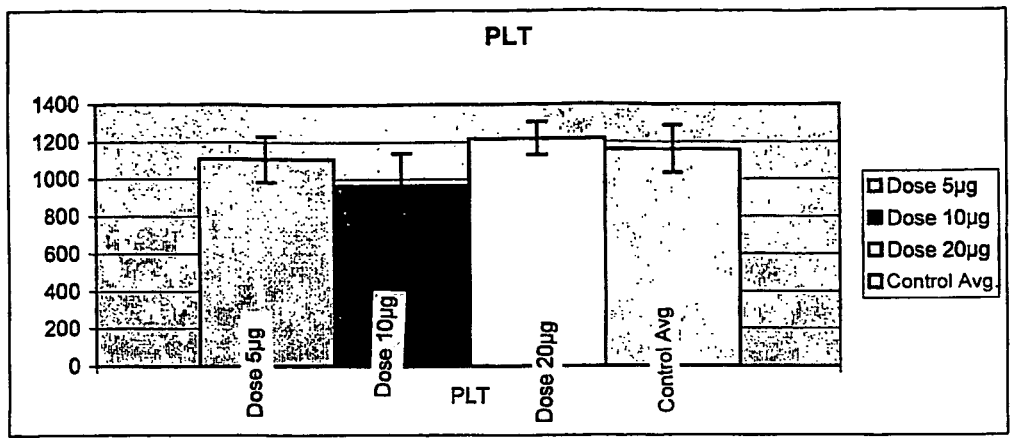

4/Isomenthone, FIGS. 9, 10A, 10B

FIG. 9 shows the percentage of inhibition of ICAM-1 expression by HUVECs at different stages of replication with 0.001% and 0.002% isomenthone following stimulation with TNF-α at a concentration of 10 ng/mL for 24 hours.

FIG. 10A shows the toxicity of isomenthone, as tested at different concentrations on HUVECs; the toxicity is given as the percentage of HUVEC endothelial cells death after 24 and 48 hours.

FIG. 10B shows the toxicity of isomenthone, as tested at different concentrations on HAECS; the toxicity is given as the percentage of HAEC endothelial cells death after 24 and 48 hours.

FIGS. 11-25 depict the in vivo toxicity study for the natural and synthetic forms (respectively "NAT" and "SYN") of geranyl acetate—a molecule called "AISA 5201" and selected for its representativeness of the AISA class—in a mouse model, for blood cell count parameters, at concentrations of 5, 10, 25, and 50 µg/mouse which correspond to non-toxic in vitro concentrations, allowing the desired biological effect to be observed, i.e. the inhibition of endothelial adhesion and endothelial actin polymerisation.

EXAMPLE 1

The tests were carried out on endothelial cells of different origins (from the umbilical vein (HUVEC), from dermal microvessels (HMVEC), and from the aorta (HAEC)) which were subjected to different stresses ($H_2O_2$, Tumour Necrosis Factor-alpha (TNF-α) for 2, 6, 24 and 48 hours), inducing activation of these cells. Activation was measured by analysing the expression of markers such as ICAM-1, VCAM-1 (Vascular Adhesion Molecule-1), using the following three techniques: ELISA assay, flow cytometry, and confocal fluorescence immunomicroscopy.

EXAMPLE 2

ELISA Enzyme Immunoassay

After stimulation with TNF-α, cells were washed with PBS and fixed with 2% formaldehyde for 10 minutes. Non-specific binding sites were then blocked with 5% skimmed milk. Cells were incubated with an anti-ICAM-1 primary antibody (R&D) at 0.02 µg/mL for two hours at room temperature and then washed five times with PBS. They were then incubated with the detection complex, an anti-mouse IgG-alkaline phosphatase conjugate (Chemicon, Euromedex) for one hour at room temperature, and then washed five times with PBS. Colorimetric detection was performed with the alkaline phosphatase substrate, 1 mg/mL paranitrophenylphosphate. The reaction was stopped after 20 min incubation with 1 M NaOH. Readings were made using a plate reader at 405 nm.

Flow cytometry also measures the expression of proteins labelled with a specific antibody carrying a fluorescent label. ELISA provides overall measurement of the expression of adhesion molecules, whereas flow cytometry can optionally discriminate between sub-populations with variable expression profiles. Cells were washed with PBS containing 0.5-2% bovine serum albumin, and then resuspended in a PBS-BSA solution containing an optimal concentration of anti-adhesion molecule antibody conjugated to a fluorophore. After washing, the cell suspension was run on the flow cytometer, which measures the specific fluorescence associated with the antibody used for labelling. Alternately, cells could be subjected to post-fixation (with PBS-BSA containing 2% paraformaldehyde) after the final washing stages, with the aim of making a delayed measurement within the next seven days.

EXAMPLE 3

Confocal fluorescence immunomicroscopy is a method for simultaneously displaying the actin network (using rhodamine-conjugated phalloidin) and ICAM-1 or VCAM-1 adhesion molecules by labelling with an FITC-conjugated antibody in vascular endothelial cells. Replicative senescence is associated with changes in the interaction between adhesion molecules and the actin cytoskeleton in vascular endothelial cells; this measurement evaluates such changes. Cells were grown on glass cover slips in culture wells. After stimulation for 2, 6, or 24 hours with TNF-α, cells were washed in PBS and fixed with 2% paraformaldehyde. Non-specific antibody binding sites were then blocked with 50 mM ammonium chloride, and cells were then permeabilised with 0.01% saponin. The cover slips with the fixed cells were then contacted with the primary antibody, FITC-conjugated anti-ICAM-1 (Diaclone), and rhodamine (Sigma P1951 phalloidin-TRITC) for 1.5 hours, and then washed twice with PBS. In the case of labelling with VCAM-1, the cells were contacted with the primary antibody, anti-VCAM-1 (Immunotech), for 1.5 hours, and then washed twice with PBS. Cells were then incubated with the secondary fluorescent anti-mouse Ig antibody, a fluorescein-labelled whole antibody (Amersham), and rhodamine (Sigma P1951 phalloidin-TRITC) for 1.5 hours, and then washed twice with PBS. Cover slips were then embedded in glycerol on slides, and observed by optical or confocal microscopy.

These techniques allow the identification of a vascular endothelial cell entry into the replicative senescence phase characterized by the irreversibility of actin polymerisation associated with the irreversible overexpression of adhesion molecules induced by the physiological replication process and/or inflammatory stress, mimicked in these tests by stimulation with TNF-α and/or $H_2O_2$.

The tests described in Examples 2 and 3 make it possible to characterize and to quantify the ability of a molecule to inhibit adhesion molecule expression and actin polymerisation, which corresponds to a reversal of the vascular endothelial cell's senescent phenotype.

EXAMPLE 4

Preliminary Toxicity Study in a Wild-Type Mouse Strain Using Different Concentrations of the Molecule Corresponding to the Concentrations Used In Vitro Based on the in vitro results obtained previously, preliminary in vivo studies were performed on the possible toxicity and functional properties of the geranyl acetate molecule called here "AISA 5201".

The acute toxicity of the synthetic molecule is known. In rats, the $LD_{50}$ is 6,330 mg/kg, with various changes in behaviour which range from drowsiness to coma.

For this preliminary toxicity study, a mouse strain called "C57/BL6" was used. This strain is known for its $LD_{50}$ for bacterial LipoPolySaccharide (LPS) of 600 µg/mouse ("Lipopolysaccharide-Induced Cytokine Cascade and Lethality in Ltα/TNFα-Deficient Mice", F. Amiot et al. 1997, *Molecular Medicine*, 3, 12, 863-874), which corresponds to a $LD_{50}$ of 3,000 mg/kg.

Two methods were used, one with the synthetic form named herein "SYN" (SIGMA catalogue number 173495), and the other with the natural unfiltered form (derived from geranium essential oils treated by HPLC) named herein "NAT", of said molecule.

On the basis of the in vitro toxicity experiments, the "SYN" and "NAT" molecules were first tested on C57/BL6 mice at concentrations of 10, 25, and 50 µg/mouse, as well as on a control batch which was injected with PBS, either via the IP (intraperitoneal) or retro-orbital (IV) routes. Each batch consisted of 4 animals. A total of 16 animals was used.

Following the experiment, a blood cell count was performed using the Cell Dyn Systems 3500/3700 machine from Abbott Laboratories. This test was carried out to reveal any possible functional alterations. The results of this experiment showed that, for both the "NAT" and "SYN" forms of the molecule, the most appropriate concentration was 50 µg/mouse because the values obtained for white blood cell (WBC, NEU, LYM, MONO) and platelet (PLT) markers were closest to those of the control batch. Moreover, red blood cell (RBC, HGB, and HTC) markers were stable at all concentrations tested (FIGS. 11-15).

A second experiment was performed using the synthetic molecule alone, at concentrations of 5, 10, and 20 µg/mouse, plus one control batch, with again 4 animals per batch, administered solely via the IP route.

Then, following the experiment, a blood cell count was carried out. The results (FIGS. 16-20) demonstrate that the "SYN" molecule is stable at the concentrations tested, remaining within the values of the standard range.

A third experiment was performed to test the "NAT" molecule at the same concentrations as for the "SYN" molecule, but using more animals, i.e. 5 animals per batch. The results (FIGS. 21-25) demonstrate that the "NAT" molecule is stable at the concentrations tested, remaining within the values of the standard range.

The synthetic "SYN" and natural "NAT" forms of geranyl acetate, the molecule called "AISA 5201" and selected because of its representativeness of the AISA class, are comparable as regards their non-toxicity in vivo in a mouse model for blood cell count parameters at concentrations of 5, 25, and 50 µg/mouse, which correspond to non-toxic in vitro concentrations, which allow the desired biological effect to be observed, i.e. inhibition of both endothelial adhesion and endothelial actin polymerisation.

Table 1 below shows the standard values for blood cell counts in C57/BL6 mice.

TABLE 1

|  | Dose = 10 µg | Dose = 25 µg | Dose = 50 µg | Control |
|---|---|---|---|---|
| WBC range | 8.13-11.3 | 7.10-7.79 | 3.29-6.79 | 0.708-3.63 |
| NEU range | 0.907-0.816 | 1.76-1.94 | 0.476-1.46 | 0.347-0.868 |
| LYM range | 5.94-7.55 | 4.47-5.30 | 1.52-5.36 | 0.255-2.23 |
| MONO range | 0.422-0.458 | 0.519-0.725 | 0.247-0.300 | 0.089-0.286 |
| EOS range | 0.009-0.015 | 0.003-0.044 | 0.005-0.014 | 0.007-0.008 |
| BASO range | 0.044-0.076 | 0.029-0.098 | 0.033-0.057 | 0.008-0.021 |
| RBC range | 8.34-8.66 | 6.62-8.20 | 6.64-7.55 | 6.80-8.63 |
| HGB range | 13.1-13.2 | 10.3-12 | 10.3-11.4 | 10.6-12.3 |
| HCT range | 38.1-39.6 | 30.2-36.6 | 31.5-33.4 | 31.1-38.8 |
| MCV range | 44.4-45.6 | 44.6-44.6 | 43.7-44.2 | 44.8-44.9 |
| MCH range | 15-15.1 | 14.6-14.6 | 14.7-15.1 | 14.6-15.1 |
| MCHC range | 32.9-33.5 | 32.7-32.7 | 32.6-33.7 | 32.6-33.6 |
| RDW range | 15.6-16 | 16.1-17 | 15.3-16.9 | 15.8-16.5 |
| PLT range | 1,089-1,091 | 1,289-1,508 | 1,220-1,282 | 768-966 |
| MPV range | 8.71-8.87 | 8.63-8.75 | 8.32-8.65 | 8.79-9.66 |
| WIC range | 8.47-11.3 | 7.57-13.8 | 4.44-7.27 | 0.847-3.63 |
| WOC range | 7.82-8.13 | 6.58-12 | 3.29-6.46 | 0.708-2.89 |

The invention claimed is:

1. A method for treating the senescence of vascular endothelial cells induced by repeated inflammatory episodes in an individual in need thereof, which comprises administering to an individual having senescence of vascular endothelial cells induced by repeated inflammatory episodes at least one plant-origin compound of terpene type, wherein said plant-origin terpene compound is selected from the group consisting of geranyl acetate, geraniol, isomenthone and limonene and said plant-origin compound of terpene type reverses the senescent phenotype of vascular endothelial cells and wherein said individual is selected by determining in a biological sample of an individual comprising vascular endothelial cells the expression level of the adhesion molecule ICAM-1 and wherein a patient is selected when ICAM-1 is overexpressed in vascular endothelial cells.

2. The method according to claim 1, wherein said plant-origin compound of terpene type is isolated and purified or prepared by chemical synthesis.

3. The method according to claim 1, for treating the senescence of vascular endothelial cells induced by repeated inflammatory episodes resulting from the presence of cancer cells.

4. The method according to claim 1, for treating tissue degeneration associated with the senescence of vascular endothelial cells induced by repeated inflammatory episodes.

5. The method according to claim 1, for treating the senescence of dermal microvascular endothelial cells as well as tissue degeneration induced by repeated inflammatory episodes resulting from exposure to the ultraviolet sunlight, pollution, or micro-abrasion.

6. The method according to claim 1, for treating tissue degeneration induced by inflammatory episodes occurring in a chronic inflammatory or in an auto-immune pathology.

7. The method according to claim 6, wherein said chronic inflammatory or auto-immune pathology is selected from the group consisting of rheumatoid arthritis, osteoarthritis, spondylarthritis, gout, and any other form of arthritis, chronic hepatitis, ulcerative colitis, Crohn's disease, vasculitis, multiple sclerosis, psoriasis, systemic and cutaneous lupus erythematosus, and scleroderma.

8. The method according to claim 1, wherein said compound is administered topically, orally, enterally, parenterally or through inhalation.

9. A method for treating the senescence of vascular endothelial cells induced by arthrosis in an individual in need thereof which comprises administering an individual having senescence of vascular endothelial cells induced by arthrosis at least one plant-origin compound of terpene type, wherein said plant-origin terpene compound is selected from the group consisting of geranyl acetate, geraniol, isomenthone and limonene and said plant-origin compound of terpene type reverses the senescent phenotype of vascular endothelial cells and wherein said individual is selected by determining in a biological sample of an individual comprising vascular endothelial cells the expression level of the adhesion molecule ICAM-1 and wherein a patient is selected when ICAM-1 is overexpressed in vascular endothelial cells.

10. The method according to claim 9, wherein said compound is limonene.

11. The method according to claim 10, wherein said compound is administered orally.

* * * * *